United States Patent [19]
Betts et al.

[11] Patent Number: 5,913,232
[45] Date of Patent: *Jun. 15, 1999

[54] REFERENCE SOLUTION CONTAINER FOR BLOOD GAS/ELECTROLYTE MEASURING SYSTEM

[75] Inventors: Ronald E. Betts, La Jolla; Douglas R. Savage, Del Mar; Michael C. Weinzierl, San Diego, all of Calif.

[73] Assignee: SenDx Medical, Inc., Carlsbad, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/650,465

[22] Filed: May 20, 1996

[51] Int. Cl.$^6$ .................................................. G01N 33/49
[52] U.S. Cl. ............................................. 73/1.03; 436/11
[58] Field of Search .......................... 73/1 G, 1 R, 19.1, 73/1.03, 1.05; 436/9, 11, 16; 204/40.1

[56] References Cited

U.S. PATENT DOCUMENTS

| | | | |
|---|---|---|---|
| 3,874,850 | 4/1975 | Sorensen et al. | 356/40 X |
| 3,997,296 | 12/1976 | Miller | 436/9 |
| 4,003,705 | 1/1977 | Buzza et al. | . |
| 4,116,336 | 9/1978 | Sorensen et al. | 206/524.8 |
| 4,126,575 | 11/1978 | Louderback | 436/11 |
| 4,415,085 | 11/1983 | Clarke et al. | 206/526 |
| 4,649,028 | 3/1987 | Kaltenbach et al. | 422/100 |
| 4,722,904 | 2/1988 | Feil | 436/11 |
| 4,786,394 | 11/1988 | Enzer et al. | 204/401 |
| 4,871,439 | 10/1989 | Enzer et al. | 204/401 |
| 4,919,895 | 4/1990 | Heldenbrandt et al. | 436/11 X |
| 4,935,106 | 6/1990 | Liston et al. | 204/401 X |
| 4,945,062 | 7/1990 | Chiang | 436/11 |
| 4,998,431 | 3/1991 | Jippinen et al. | 73/1 G |
| 5,004,583 | 4/1991 | Buruswamy et al. | 422/58 |
| 5,061,631 | 10/1991 | Calabrese | 436/11 |
| 5,084,158 | 1/1992 | Inoue | 204/411 |
| 5,086,642 | 2/1992 | Jessel et al. | 73/1 G |
| 5,140,845 | 8/1992 | Robbins | 73/19.1 X |
| 5,230,427 | 7/1993 | Betts et al. | 206/213.1 |
| 5,279,797 | 1/1994 | Burns et al. | 422/102 |
| 5,284,568 | 2/1994 | Pace et al. | 204/403 |
| 5,293,770 | 3/1994 | Hanson et al. | 204/401 X |
| 5,328,848 | 7/1994 | Fong et al. | 436/11 |
| 5,420,038 | 5/1995 | Wall et al. | 436/11 X |
| 5,477,883 | 12/1995 | Totten | 137/614.03 |
| 5,519,635 | 5/1996 | Miyake et al. | 364/497 |
| 5,555,908 | 9/1996 | Edwards et al. | 137/329.1 |
| 5,558,985 | 9/1996 | Chiang et al. | 436/11 X |
| 5,578,194 | 11/1996 | Young et al. | 436/11 X |
| 5,665,315 | 9/1997 | Robert et al. | 204/401 X |
| 5,718,816 | 2/1998 | Savage et al. | 204/409 |
| 5,777,202 | 7/1998 | Betts et al. | 73/1.03 |
| 5,820,825 | 10/1998 | Weinzierl et al. | 422/102 |
| 5,844,200 | 12/1998 | Leader et al. | 219/121.71 |

FOREIGN PATENT DOCUMENTS

2 100 859   1/1983   United Kingdom .

Primary Examiner—Thomas P. Noland
Attorney, Agent, or Firm—Fish & Richardson P.C.

[57] ABSTRACT

A reference solution container for an analyzer for measuring gas and/or electrolyte levels in a fluid. The vessel includes a fluid container for holding a reference solution and a self-sealing fluid port for repeatedly accessing the reference solution in the fluid vessel by a fluid carrying device that is external to the reference solution container. The partial pressure of each gas in the reference solution within the fluid vessel is maintained at a substantially constant level.

5 Claims, 6 Drawing Sheets

REFERENCE SOLUTION CONTAINER FOR BLOOD GAS/ELECTROLYTE MEASURING SYSTEM

RELATED APPLICATIONS

This application is related to co-pending U.S. patent application Ser. No. 08/650,624, filed May 20, 1996, entitled "Waste Container for Portable Blood Analyzer", and now U.S. Pat. No. 5,820,825; U.S. patent application Ser. No. 08/650,340 filed May 20, 1996, entitled "Integral Fluid and Waste Container for Blood Analyzer;" U.S. patent application Ser. No. 08/650,341, filed May 20, 1996, entitled "Portable Modular Blood Analyzer with Simplified Fluid Handling Sequence," U.S. patent application Ser. No. 08/650,622, filed May 20, 1996, entitled "Blood Gas/ Electrolyte Calibrator and Method for Use," and now abandoned; U.S. patent application Ser. No. 08/648,692, filed May 16, 1996, entitled "Locking Sensor Cartridge with Integral Fluid Port Electrical Connections, and Pump Tube, and now U.S. Pat. No. 5,718,816; U.S. patent application Ser. No. 08/649,009, filed May 16, 1996, entitled "Sensors with Subminiature Through Holes and Method for Fabricating Such Sensors;" U.S. patent application Ser. No. 08/648,675, filed May 16, 1996, entitled "Electronic Wiring Substrate with Subminiature Through Holes and Method for Fabricating Such Sensors;" U.S. patent application Ser. No. 08/648,676, filed May 16, 1996, entitled "A Sensor Cartridge for an Analyte Analyzer;" U.S. patent application Ser. No. 08/648,694, filed May 16, 1996, entitled "Method and Apparatus for Drilling Subminiature Through Holes in a Sensor Substrate," and now U.S. Pat. No. 5,844,200; and U.S. patent application Ser. No. 08/649,525, filed May 17, 1996, entitled "Method and Apparatus for Ratiometric Measurement of Hematocrit," which are all assigned to the assignee of the present invention.

BACKGROUND OF THE INVENTION

1. Field of the Invention

The present invention relates to a reference solution container for a fluid analysis device. More particularly, the present invention relates to a container for a reference or calibration solution for use in a system for analyzing and measuring the gas and/or electrolyte levels in a fluid, such as blood.

2. Description of Related Art

Various fluid analysis devices are used in testing and measuring gas and/or electrolyte levels in fluids. These devices are used, for example, in medical and environmental applications to measure the gas and/or electrolyte levels in blood, urine, water, and other fluids.

Fluid analysis devices must be calibrated frequently when they are being used to test fluid samples. For example, it is preferable to recalibrate a blood analyzer after each blood sample is tested for gas and/or electrolyte levels. As a result, it is essential to provide some means of applying a reference or calibration solution to the fluid analysis devices. In many cases, a reference or calibration solution container can be coupled to the fluid analysis machine, thereby providing a ready means of recalibrating the fluid analysis machine when testing samples.

A reference or calibration container holds a reference or calibration solution that contains gases, such as oxygen and carbon dioxide, in solution at known partial pressures. Because these partial pressures are known to a relatively precise degree, the reference or calibration solution can be used to accurately calibrate the fluid analysis machine after fluid samples have been tested. Yet, such containers are frequently stored for weeks or months and are also frequently left attached to the fluid analysis machine for several weeks before they are completely depleted of reference or calibration solution and are replaced with a new container. Thus, a reference or calibration solution container must be designed such that it can reliably maintain the partial pressures of the gases in solution while the container is stored and/or attached to a fluid analysis machine.

It is also advantageous for reference or calibration solution containers to have a fluid port that is repeatedly accessible by an external fluid carrying device, such as a fluid analysis device. Multiple-access allows the reference or calibration solution container to be used for multiple tests on fluid samples and makes the container more economical and easier to use than single use containers, which must be discarded after a single recalibration. It is also desirable to provide a self-sealing mechanism on the container's repeated access port. A self-sealing, multi-access port makes the container more economical; is relatively fool-proof, in it prevents unwanted fluid loss from the container; improves the manufacturability of the container, especially in the process for filling the container; provides more rapid access to the solution; makes the container more flexible, in that ingredients can be added to the container after it has been filled with solution; and allows any head space left in the container after filling to be easily evacuated.

While existing reference or calibration solution containers do claim to maintain the partial pressures of the gases in solution, they do not provide this capability together with a multiple-access, self-sealing port.

Accordingly, a need exists for a reference or calibration solution container that maintains partial pressures of gases in solution and that can be repeatedly accessed through a self-sealing fluid port by an external fluid carrying device. The present invention provides such a container.

SUMMARY OF THE INVENTION

The present invention is a reference or calibration solution container for a fluid analysis device, such as a blood analyzer. The container of the present invention can be used in a variety of applications in which a fluid analyzer must be recalibrated after performing tests on a fluid sample. The container of the present invention can be used in a variety of medical applications as well as in environmental applications in which fluids are being analyzed for gas and/or electrolyte content. Examples of fluids for which the container can be used include blood, water, urine, spinal fluid, and semen.

For convenience, throughout the remainder of this description, the container of the present invention will be described with reference to blood analysis devices and blood samples. It should be understood, however, that the container is not limited to such applications and has a much broader field of use, at least in the applications and with the exemplary fluids set forth above. Furthermore, for convenience, the container of the present invention will be referred to throughout the remainder of this description as a "reference solution container." It should be recognized, however, that the term "reference solution" is intended to encompass calibration solutions and that the container of the present invention can be used for calibration solutions.

The reference solution container of the present invention can be used in a blood analyzer that measures gas and/or electrolyte levels in blood. The container includes a fluid vessel for holding a reference solution and a self-sealing fluid port for repeatedly accessing the reference solution in the fluid vessel by an external fluid carrying device. The reference solution container substantially maintains a partial pressure of gases (such as oxygen and carbon dioxide) in the reference solution. The external fluid carrying device may be part of the blood analyzer, and the reference solution container can be secured to the blood analyzer, such that the external fluid carrying device engages the self-sealing fluid port for repeated access to the reference solution by the blood analyzer. The container may be incorporated into a calibration cartridge that can be secured to the blood analyzer.

The fluid vessel is preferably flexible and is made from metal-plastic laminate material (such as aluminum foil with an interior layer of heat sealable plastic, as is known). The flexible fluid vessel may include a flexible protective layer (such as foam) covering a substantial portion of the exterior of the fluid vessel. The protective layer helps to prevent damage to the vessel by punctures or holes. The vessel may have substantially zero head space in its interior.

The self-sealing fluid port on the reference solution container is preferably a two-way valve (such as a poppet valve) that permits fluids to exit and enter the fluid vessel when the valve is engaged by an external fluid carrying device. The fluid port may have a port body, with a fluid communication path extending throughout its length, that has a fitting end for engaging the external fluid carrying device. A self-sealing valve element, located substantially within the fluid communication path, substantially prevents fluid flow into and out of the fluid vessel unless the external fluid carrying device is engaging the self-sealing valve. The self-sealing valve element may include a valve stem and a valve stop, such that the valve stop forces the valve stem against a sealing surface to substantially prevent fluid flow through the fluid communication path, unless the external fluid carrying device is inserted into the fluid communication path and deflects the valve stem from the sealing surface.

The reference solution container may be filled with reference solution such that it has an internal pressure that is greater than the ambient atmospheric pressure at sea level. Preferably, the internal pressure of the fluid vessel is at least about 1.01 times the ambient atmospheric pressure at sea level. In such over-filled reference solution containers, it is desirable to provide a protective layer, because over-filling makes the containers more susceptible to bursting and puncturing.

The details of the preferred embodiment in the present invention are set forth in the accompanying drawings and the description below. Once the details of the invention are known, numerous additional innovations and modifications will become obvious to one skilled in the art.

DETAILED DESCRIPTION OF THE INVENTION

Throughout this description, the preferred embodiment and examples shown should be considered as exemplars, rather than as limitations on the present invention.

I. Overview

Figure 1:
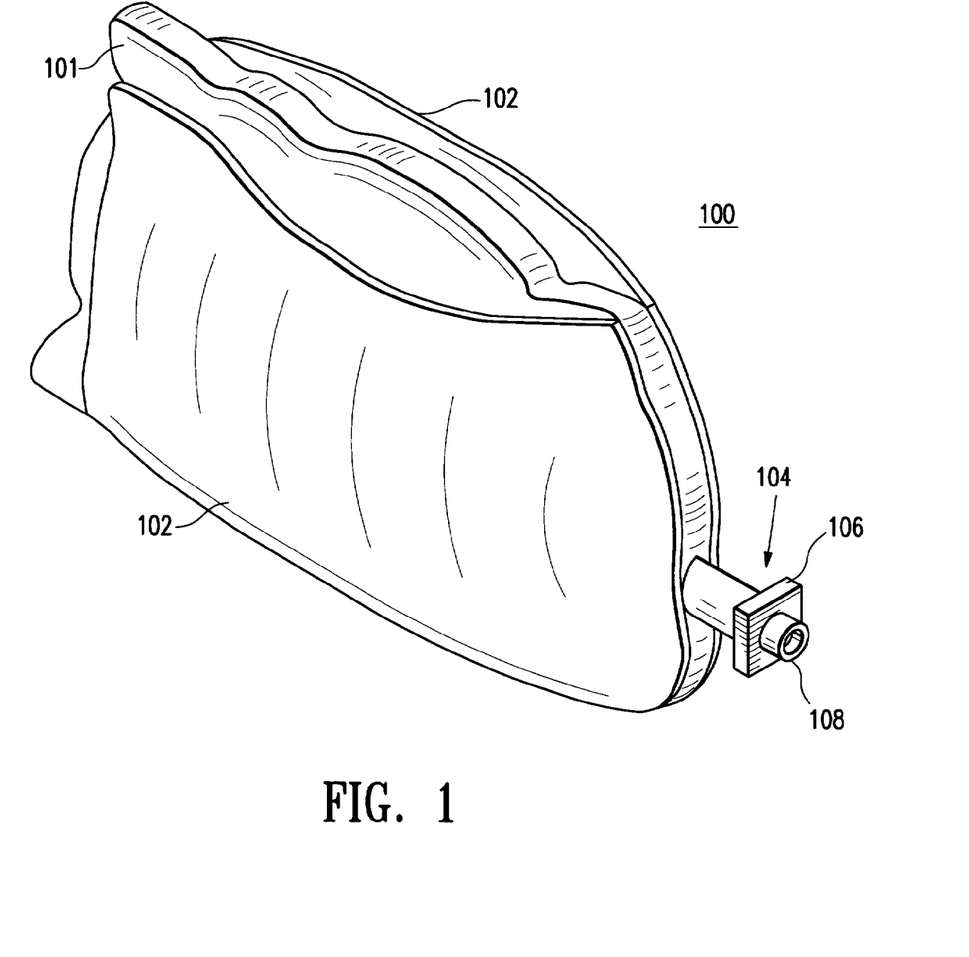
FIG. 1 is a perspective view of a flexible reference solution container of the present invention, in which the container is filled to an internal pressure greater than ambient, and showing a protective layer.

FIG. 1 is a perspective view of a reference solution container 100 in accordance with the present invention. The container 100 holds a reference solution for use in calibrating fluid analysis devices, such as a blood analyzer. The reference solution container 100 has a fluid vessel (or bag) 101 and a self-sealing fluid port 104 for repeatedly accessing the reference solution in the fluid bag 101 by a fluid carrying device (not shown) that is external to the reference solution container. (The fluid vessel 101 will be referred to throughout the remainder of this description primarily as a "fluid bag," because, in the preferred embodiment, the fluid vessel 101 is a flexible, metal-plastic laminate, "bag." It should be understood, however, that the fluid vessel 101 is not intended to be limited to a flexible bag.) The fluid port 104, which will be described in detail below, has a flange 106, a port body 108 for engaging the external fluid carrying device, and a fluid communication port 110. The container 100 may optionally also have a protective layer 102 covering a substantially portion of the exterior of the container 100.

Preferably, the fluid bag 101 is made from a flexible material, preferably an aluminum foil-plastic laminate, and may be filled to an internal pressure that is greater than the ambient atmospheric pressure at sea level surrounding the container 100. (For convenience, a reference solution container that is filled to a greater internal pressure than ambient will be referred to for the remainder of this description as an "over-filled container.") In accordance with this invention, an over-filled container is defined as a reference solution container that is filled to an internal pressure at least about 1.01 times greater than the ambient surrounding pressure at sea level.

The protective layer 102 can be secured to the exterior surface of the fluid bag 101. Preferably, the protective layer is an adhesive-backed foam that is adhered to the fluid bag 101 before it is filled with reference solution. The protective foam 102 may alternatively be applied after the fluid bag 101 is filled. It is desirable to cover substantially all, but not the entirety, of the exterior of the fluid bag 101, in order to maintain a sufficient amount of flexibility in the fluid bag 101 to allow it to contract as it is emptied of reference solution. Either one, two, or more pieces of protective layering (or patches of such layering) can be applied to the container 100, depending on the configuration and size of the fluid bag 101 as well as the desired amount of protection and flexibility of the fluid bag 101.

The protective layer 102 is especially important for an over-filled container. Because such containers are filled to a relatively high internal pressure, they are subject to puncturing from sharp objects and to the formation of pin holes from vibration and motion. The protective layering 102 also facilitates over-filling of the fluid bag 101, because the layering 102 provides additional structural integrity and strength to the (preferably flexible aluminum) fluid bag 101 to reduce the chance of it bursting during filling. It should be understood, however, that the protective layering 102 is not limited to over-filled containers, but rather can be used on any reference solution container for which it is desirable to protect the container from puncturing, tearing, and rupturing. The protective layer 102 has a thickness of at least about 0.005". The protective layer 102, however, may be thicker than 0.005" to provide even greater protection. The layer 102, however, is preferably not so thick that it renders the fluid bag 101 rigid.

The protective layer 102 can alternatively be a protective vinyl (or other suitable) coating. Such a coating is preferably applied by submerging the fluid bag 101 in the coating while it is in a liquid state. When the fluid bag 101 is removed, the coating then dries and forms a protective layer on the fluid bag 101. The coating could optionally be sprayed in a liquid state onto the fluid bag 101, after which the coating similarly dries, forming a protective layer.

II. Cartridge and Blood Analysis Machine

Figure 2A:
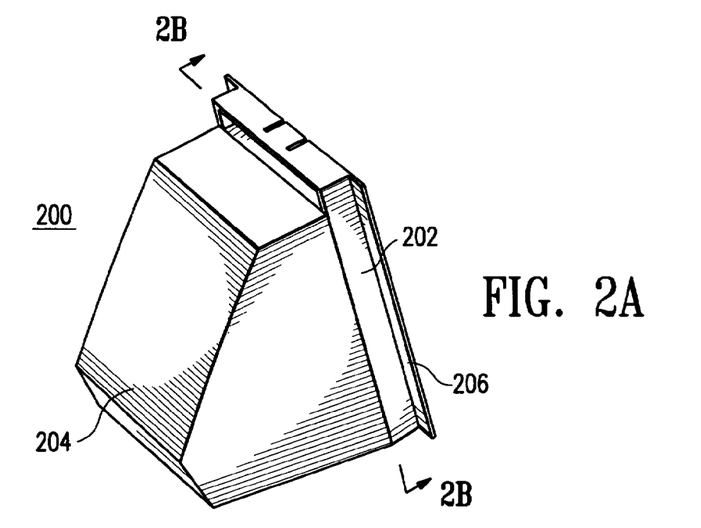
FIG. 2A is a perspective view of a container cartridge for holding the reference solution container of the present invention.
Figure 2B:
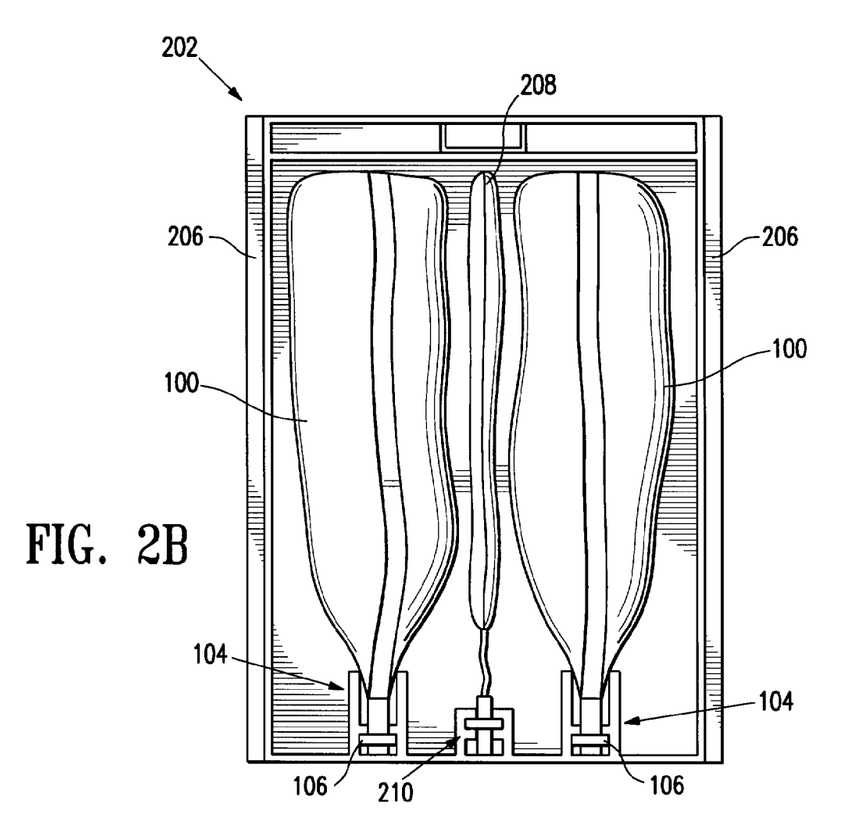
FIG. 2B is a cut-away view of the container cartridge of FIG. 2A along line 2B—2B.

FIG. 2A shows a cartridge 200 that can be employed to hold one or more reference solution containers 100. The cartridge 200 may have a tray 202 and cover 204 that are secured together to enclose the containers 100. The cartridge illustrated in FIG. 2 is merely exemplary. It should be recognized that the cartridge 200 may have almost any shape and need not completely enclose the containers 100. The cartridge may have at least one rail 206 for aligning the cartridge 200 with a housing for a blood analysis device, as will be described with reference to FIG. 3. The cartridge 200 may be made from plastic or any other suitable material. A more detailed description of an exemplary cartridge can be found in a U.S. Patent Application entitled "Integral Fluid and Waste Container for Blood Analyzer," assigned to the assignee of the present application and referenced above.

FIG. 2B is a cut-away view of the cartridge 200 along line 2B—2B of FIG. 2A. This view shows the tray 202 holding two reference solution containers 100 and a waste bag 208. The waste bag 208 collects waste fluids (such as blood and used reference solution) from the blood analysis device. The waste bag 208 has a waste fluid port 210, which is preferably a one-way valve that only permits waste fluids (and gases) to enter the waste bag 208. The reference solution containers 100, being preferably flexible, contract as reference solution exits the containers 100. As the containers 100 contract, they leave a void in the cartridge 200. This void may be filled by the waste bag 208 as it expands with waste fluid. Preferably, the waste bag 208 may contain a moisture absorbent material that converts the incoming waste fluid into a substantially solid material. A more detailed description of a waste bag can be found in a U.S. Patent Application entitled "Waste Container for Portable Blood Analyzer," assigned to the assignee of the present application and referenced above.

Figure 3:
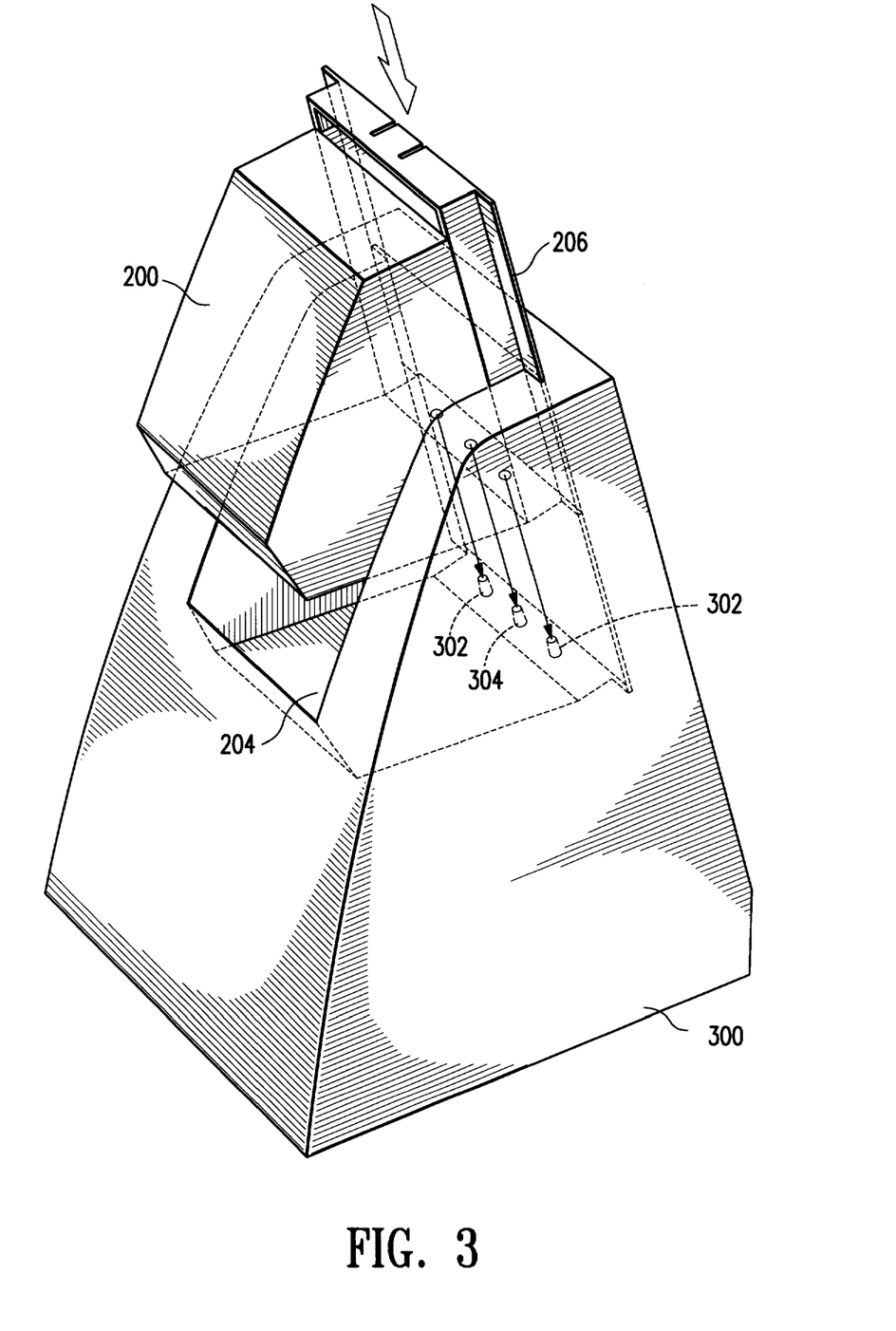
FIG. 3 shows the cartridge of FIG. 2 secured within a blood analysis device.

FIG. 3 shows the housing of a blood analyzer 300 with the cartridge 200 inserted into a cavity in the blood analyzer 300. The rails help guide the cartridge 200 into the blood analyzer 300, such that the fluid port 104, 210 for the reference solution bags 100 and waste bag 208 will properly engage fluid carrying devices (or fittings) 302, 304 that are part of the blood analyzer 300. Fluid fittings 302 are positioned on the blood analyzer 300 to engage the fluid ports 104 on the reference solution bags 100, and fluid fitting 304 is positioned to engage the fluid port 210 on the waste bag 208. The fluid fittings 302, 304 protrude from and are part of the blood analyzer 300. As such, the fittings 302, 304 constitute fluid carrying devices that are external to the reference solution containers 100 and the waste bag 208. A more detailed description of an exemplary blood analyzer can be found in a U.S. Patent Application entitled "Portable Modular Blood Analyzer with Simplified Fluid Handling Sequence," filed concurrently with this application, assigned to the assignee of the present application, and referenced above.

III. Self-Sealing Fluid Port

FIGS. 4A—4F illustrate an exemplary embodiment of the self-sealing fluid port 104. Because the reference solution container 100 can be used for calibrating devices used to measure gases in fluids, such as blood, the self-sealing fluid port 104 is preferably substantially gas-tight. The substantially gas-tight seal helps to maintain the partial pressure of the gases (such as oxygen and carbon dioxide) in solution within the container 100. The self-sealing feature of the fluid port 104 helps attain a gas-tight seal, because each time the external fluid carrying device 302 is disengaged from the fluid port 104, the fluid port automatically reseals. The fluid port 104 is also preferably directly coupled (without external plastic tubing, or the like) to the external fluid carrying device 302 to help prevent any appreciable loss of gases in the reference solution through external plastic tubing, gas-permeable fitting, and the like, connecting the fluid port 104 to an external fluid carrying device.

In the preferred embodiment of the reference solution container 100, the self-sealing fluid port 104 is a two-way valve. When engaged by an external fluid carrying device, the container 100 can be filled with reference solution via the fluid port 104. Additional reference fluid or other ingredients can also be added to the container 100 via the fluid port 104 after the initial filling. Then, when the container 100 is filled, the solution within the container 100 can be accessed by an external fluid carrying device to drain the container 100 and calibrate a fluid analysis device.

Figure 4A:
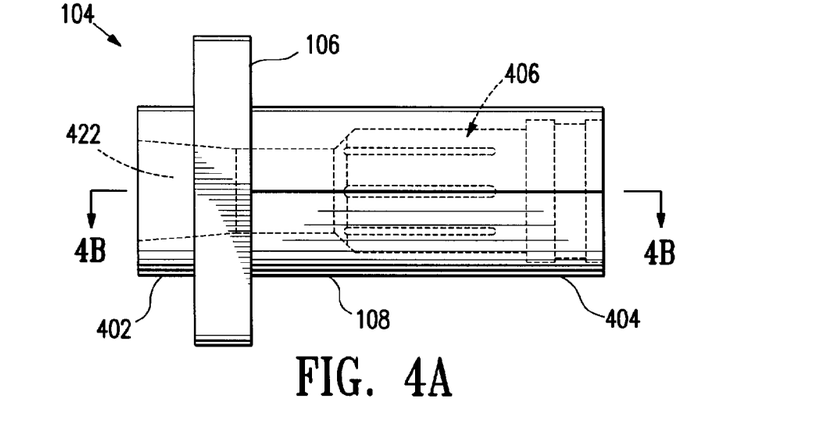
FIG. 4A is a side-view of an exemplary self-sealing fluid port coupled to a fluid vessel of the present invention.

FIG. 4A is a side-view of the preferred self-sealing fluid port 104 of the present invention. The fluid port 104 has a port body 108, a flange 106, a fitting end 402, a bag end 404, a fluid communication path 422, and a self-sealing valve assembly 406. The self-sealing valve assembly 406 is located within the fluid communication path 422, which is coaxial with the port body 108. The flange 106 substantially surrounds the port body 108, the two elements preferably being an integral assembly formed from polypropylene. Those skilled in the art will recognize that, while polypropylene is the preferred material, other suitable materials exist.

Figure 4B:
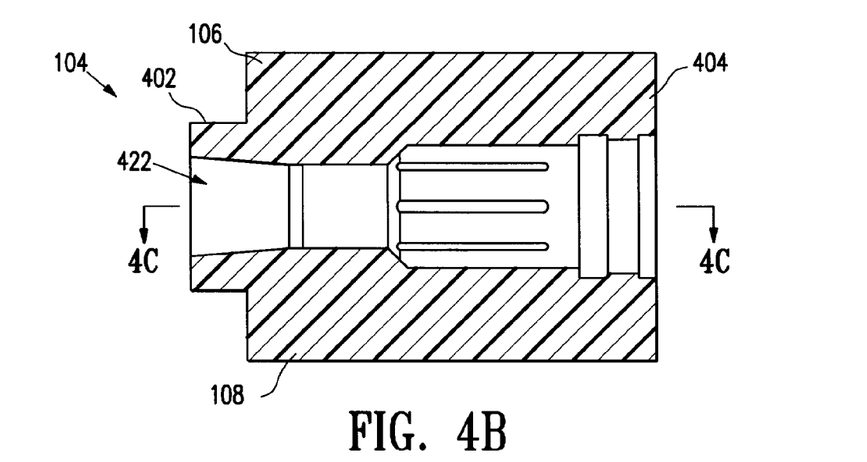
FIG. 4B is a cut-away view of the self-sealing fluid port along line 4B—4B.

FIG. 4B is a cut-away view of the self-sealing fluid port 104 along line 4B—4B in FIG. 4A. The view of FIG. 4B shows that the bag end 404 is asymmetrical in shape, as it is wider in one cross section (FIG. 4B) than in the other (FIG. 4A). Preferably, if the reference solution container 100 is a bag made from a flexible aluminum material, the bag end 404 is substantially elliptical in shape, for thermally-sealing the bag 100 to the fluid port 104. An elliptical shape facilitates a stronger thermal seal between the bag 100 and the port 104. If thermally sealed, the material from which the fluid port 104 is made should be compatible with the melting characteristics of the material (e.g., aluminum-plastic laminate) forming the bag 100. Alternatively, the fluid port 104 and the bag 100 can be adhesively coupled to one another. FIG. 4B also shows that, from this view, the flange 106 and the bag end 404 have the same dimensions.

Figure 4C:
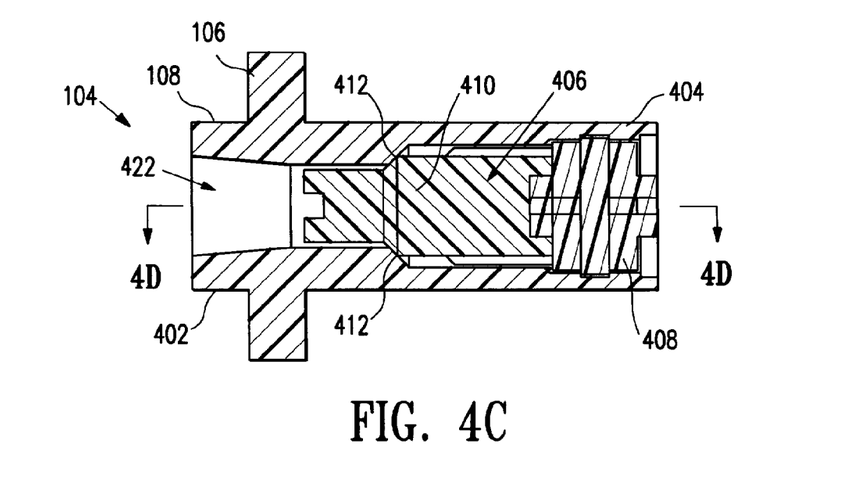
FIG. 4C is a cut-away view of the self-sealing fluid port along line 4C—4C, showing a self-sealing valve assembly within the port.

FIG. 4C is a cut-away view of the self-sealing fluid port 104 along line 4C—4C in FIG. 4B showing the self-sealing valve assembly 406. The assembly is preferably a poppet valve, including a stem backstop 408 and a stem 410, the latter preferably being made of silicone. When a fluid fitting 302 (preferably a Luer fitting) is inserted into the fluid communication path 422, the fitting 302 engages the silicon stem 410 (which is compressible), forcing the stem 410 back against the stem backstop 408, which is secured in place within the fluid communication path 422 of the port body 108. The silicon stem 410 is thus pushed rightward (with reference to FIG. 4C) until a gap forms between the stem 410 and bevels 412. This creates an opening through the fluid communication path 422 to the stem backstop 408, which has channels through which fluid can flow, thereby allowing fluid flow through the self-sealing fluid port 104 and out of the reference solution container 100.

When the external fluid carrying device 302 is removed from the fluid communication path 422 of the self-sealing fluid port 104, the resilient silicon stem 410 expands leftward (with reference to FIG. 4C), resealing the gap between the stem 410 and the bevels 412, thereby preventing further fluid flow through the fluid communication path 422. Thus, in the preferred embodiment, the fluid port 104 is self-sealing, so that, when the external fluid carrying device 302 is removed from the fluid port 104, no appreciable amount of fluid will exit the reference solution bag 100.

Figure 4D:
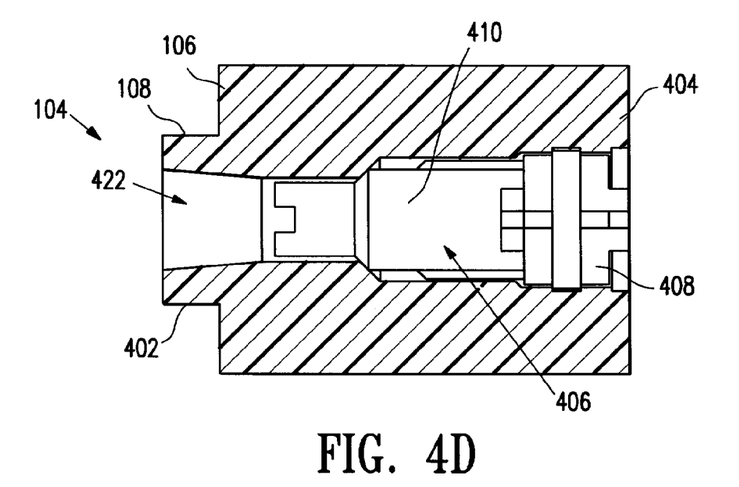
FIG. 4D is a top cut-away view of the self-sealing fluid port along line 4B—4B, showing the self-sealing valve assembly and an elliptical shape on the end of the port that engages the fluid vessel.
Figure 4E:
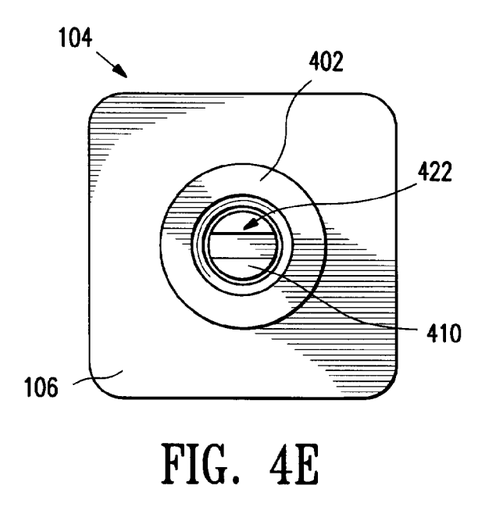
FIG. 4E is a front view of the self-sealing fluid port, showing a flange on the port.
Figure 4F:
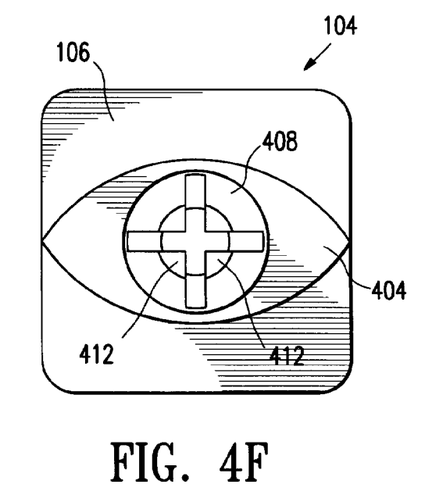
FIG. 4F is a rear view of the self-sealing fluid port.

FIG. 4D is a top cut-away view of the fluid port 104 along line 4D—4D in FIG. 4C showing the self-sealing valve 406 with respect to the preferred elliptical bag end 404. FIG. 4E is a front view of the fluid port 104 showing that the flange 106 is preferably rectangular in shape and showing the front of the valve stem 410 within the fluid communication path 422. FIG. 4F is a rear view of the fluid port 104, showing the elliptical shape of the bag end 404 and the rear of the stem backstop 408 within the fluid communication path 422. As can be seen, the stem backstop 408 has spaces (or channels) 412 through which fluid can flow.

IV. Characteristics of the Reference Solution Container

The reference solution container 100 of the present invention maintains a substantially constant partial pressure level of each gas in solution within the container 100 for substantially the life of the container 100. The reference solution within the container 100 contains at least one gas having a partial pressure. For example, the reference solution may contain oxygen and carbon dioxide gases as well as other gases. It is important to maintain the partial pressure of each gas in solution, because, if the partial pressures are not maintained at a substantially constant level, the reference solution cannot be used to calibrate the blood analysis device 300; the solution will inaccurately recalibrate.

Tests have been run with the container 100 of the present invention to demonstrate that the partial pressure of the gases in the container 100 remain substantially constant for a sufficient duration to give the container 100 a reasonable shelf life and a reasonable lifespan when in use on the blood analysis device 300. In the first test, a preferred composition of Reference Solution I, prepared at 37 degrees Celsius and at atmospheric pressure tonometered with 5% $CO_2$, 20% $O_2$, and the balance of $N_2$, is as follows:

TABLE 1

| Compound | Concentration | |
|---|---|---|
| Buffer, 3-Morpholinopropane-Sulfonic Acid (MOPS) | 4.1 | mmol/liter |
| Buffer, NaMOPS | 12.6 | mmol/liter |
| KCl | 3.5 | mmol/liter |
| NaCl | 108 | mmol/liter |
| $NaC_2H_3O_2$ | 10 | mmol/liter |
| $NaHCO_3$ | 20 | mmol/liter |
| $CaCl_2$ | 1.6 | mmol/liter |
| Glutaraldehyde (25% wt./vol.) | 0.63 | ml/liter |
| Water | 1.0 | liter |

The reference compositions were prepared by premixing all of the constituents, followed by tonometering the solution at 37 degrees Celsius and ambient atmospheric pressure with oxygen and $CO_2$ mixed with nitrogen to produce the desired level of $pCO_2$, $PO_2$, and pH for the solution. The resulting solution was transferred substantially gas-tightly into substantially evacuated foil fluid bags 101 through the self-sealing fluid port 104 of the present invention. The resulting packages contain Reference Solution I showing a pH of approximately 7.4, $pCO_2$ of approximately 33 mmHg, and $PO_2$ of approximately 145 mmHg and are suitable for blood-gas calibrating/control solutions. Electrolytes used in this solution have the approximate measured values, $K^+3.3$ mM/liter, $Na^+144$ mM/liter, $Ca^{++}1.35$ mM/liter, and $Cl^-110$ mM/liter, which can be used for calibration/control of the corresponding electrolyte sensor in the blood analyzer 300.

In the second test, a preferred composition of Reference Solution II, prepared at 37 degrees Celsius and at atmospheric pressure tonometered with 10% $CO_2$, 20% $O_2$, balance $N_2$ gas, is as follows:

TABLE 2

| Compound | Concentration | |
|---|---|---|
| Buffer, 3-Morpholinopropane-Sulfonic Acid (MOPS) | 14.1 | mmol/liter |
| Buffer, NaMOPS | 12.6 | mmol/liter |
| KCl | 8.9 | mmol/liter |
| NaCl | 86 | mmol/liter |
| $NaC_2H_3O_2$ | 10 | mmol/liter |
| $NaHCO_3$ | 20 | mmol/liter |
| $CaCl_2$ | 4.9 | mmol/liter |
| Glutaraldehyde (25%) | 0.63 | mmol/liter |
| Water | 1.0 | liter |

When Reference Solution II was prepared in a similar manner to Reference Solution I (described above), the resulting packages contain reference solution showing a pH of approximately 7.0, $pCO_2$ of approximately 65 mmHg, and $PO_2$ of approximately 150 mmHg. Electrolytes used in this solution have the approximate measured values: $K^+8.7$ mM/liter, $Na^+122$ mM/liter, $Ca^{++}4.1$ mM/liter, and $Cl^-99$ mM/liter.

The stability of reference solutions packaged in the manner described above for Reference Solutions I and II is shown in Table 3 below. In these examples, 14 packages each from Lot A and Lot B were repeatedly tested using two blood gas analysis instruments. Overall average values and standard deviations were calculated for $O_2$ and $CO_2$ at the sampling times indicated.

TABLE 3

| Time (days) | CO$_2$ mmHg | | O$_2$ mmHg | S.D. |
|---|---|---|---|---|
| | | LOT A | | |
| | | Standard Dev. (S.D.) | | |
| 0 | 32.9 | 0.4 | 148.6 | 1.5 |
| 49 | 32.5 | 0.3 | 145.0 | 1.2 |
| 80 | 32.4 | 0.2 | 145.9 | 1.6 |
| 97 | 32.3 | 0.3 | 146.5 | 1.1 |
| | | LOT B | | |
| | | S.D. | | |
| 0 | 32.7 | 0.6 | 147.2 | 1.2 |
| 57 | 32.2 | 0.4 | 144.8 | 1.6 |
| 75 | 32.2 | 0.4 | 145.7 | 1.7 |
| 92 | 32.0 | 0.5 | 145.4 | 2.2 |

It is believed that compositions of Reference Solutions I and II can be tonometered at temperatures other than 37 degrees Celsius and with gas concentrations other than 10% or 5% CO$_2$ and 20% O$_2$, the balance N$_2$.

Figure 5:
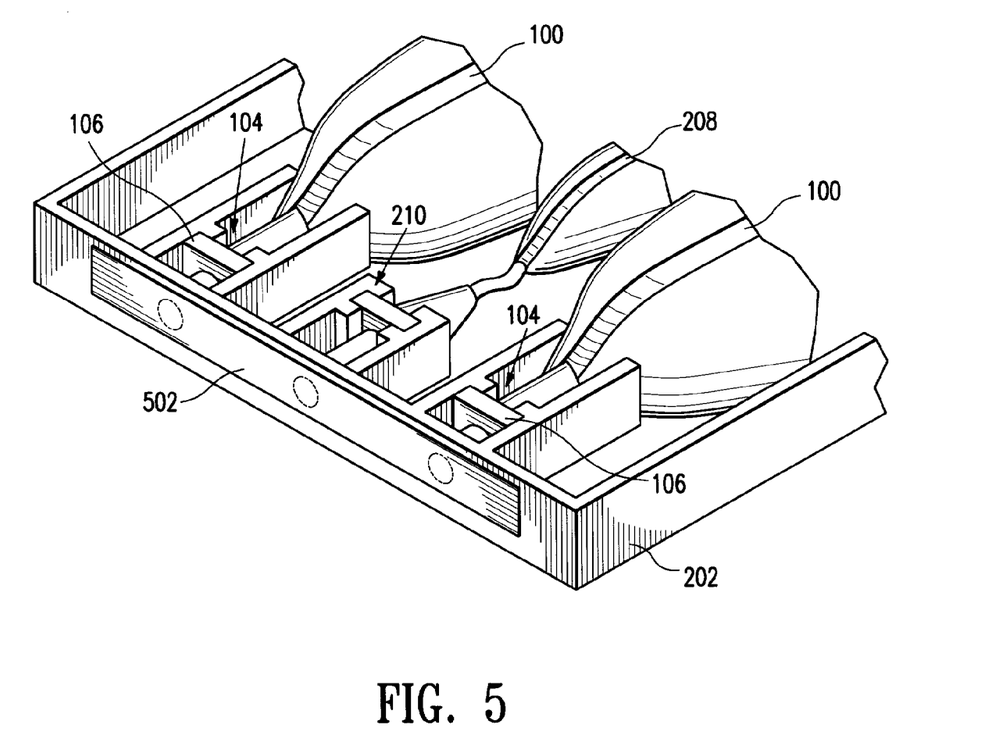
FIG. 5 shows a foil tape secured to the self-sealing fluid ports of two reference solution containers and a waste container.

To increase the shelf life of reference solutions packaged in the reference solution container 100, or if it is necessary to have gas concentrations varying widely from ambient, the self-sealing fluid port (or valve) 104 on a reference solution container 100 may be covered with an aluminum (or foil) material 502. The foil tape 502 protects the valve 104 and further prevents the communication of gas through the valve 104 during transport and storage of the container 100. A metallized tape such as 3M No. 425 aluminum foil tape over the valve 104 results in improved stability of the reference solution within the container 100. Table 4 shows test results for reference solutions Lot C, containing pCO$_2$ of 63 mmHg packaged without foil tape 502, and Lot D, containing pCO$_2$ of 66.2 mmHg packaged with foil tape 502.

TABLE 4

| Time (days) | CO$_2$ mmHg | S.D. |
|---|---|---|
| | LOT C | |
| 0 | 63 | 0.4 |
| 72 | 57 | 0.5 |
| | LOT D | |
| 0 | 66.2 | 0.6 |
| 63 | 66.6 | 0.6 |

As can be seen in Table 4, Lot D, which was equipped with foil tape 502, remains more stable for a longer period of time than Lot C, which did not include foil tape 502.

FIG. 5 shows tray 202 with foil tape 502 covering the self-sealing fluid ports (or valves) 104 and waste fluid port 210. It should be understood, however, that the foil tape 502 need not be a single piece, like that shown in FIG. 5, but instead could be independent pieces covering each port from which it is desirable to protect against the escape of gases and to prevent dirt from interfering with the valves 104, 210. When the cartridge 200 is ready to be inserted into the blood analyzer 300, the foil tape 502 is preferably first removed, although the cartridge 200 can be inserted into the analyzer 300 with the foil 502 in place, and the fittings 302, 304 would then puncture the foil tape 502 when inserted into the valves 104, 210. Those skilled in the art will recognize that the foil tape 502 is merely an exemplary means by which the self-sealing valves 104, 210 can be further sealed against the escape or ingress of gases. Other means include metal or plastic plugs or caps.

With the foil tape 502 in place, the reference solution containers 100 are even further substantially sealed against the communication of gases through the valve 104.

A reference solution container 100 may be filled with reference solution to an internal pressure greater than ambient. By over-filling the reference solution container 100 with reference solution, the container 100 can hold more reference solution than conventional containers, which are filled to an internal pressure less than or equal to the ambient atmospheric pressure. The ability to hold more reference solution means the over-filled reference solution container 100 lasts longer and need not be replaced as often as a conventional bag. This results in more blood tests per container 100.

Over-filling the reference solution container 100 also reduces the susceptibility to barometric pressure changes of the gases in solution within the over-filled container 100. Thus, the tonometry level of those gases is maintained at a substantially constant level.

It is believed that the structural relationship of the reference solution containers 100, the waste bag 208, and the cartridge 200 help maintain the tonometered state of the oxygen gas and maintain the pressure level within the sealed containers 100 for substantially all of their lifetime, even when changes occur in the barometric pressure surrounding the containers 100. The containers 100, when full of reference solution, and the empty waste bag 208, preferably fit relatively snugly within the cartridge 200. Thus, during transport and storage (e.g., when the cartridge 200 has not been used), the reference solution containers 100 are constrained by the walls of the cartridge 200. As the containers 100 are emptied during blood is tests, the void they leave within the cartridge 200 from their decreasing internal volume is filled by the expanding waste bag 208, which holds the waste blood and waste reference solution from the blood analyzer 300. Accordingly, the reference solution containers 100 remain constrained, now by the walls of the cartridge 200 and the expanding waste bag 208, as the reference solution containers 100 are emptied of reference solution.

Further, a relatively small amount of head space (e.g., air) may be maintained within the reference solution bags 100. Because the fluid bag portion 101 of the containers 100 is preferably made from an aluminum-plastic laminate material, some oxidation may occur within the fluid bag 101, thereby reducing the amount of oxygen gas in solution within the fluid bag 101. Oxygen gas in the head space may replenish the oxygen gas lost from the reference solution. The amount of head space within the fluid bag 101 is no more than about 5% of the overall internal volume of the bags 101 and is preferably in the range of about 0.01% to about 0.1% of the internal volume.

It has been experimentally observed that the reference solution containers 100 of the present invention maintain the internal tonometered gases at substantially the same partial pressure levels for most of the lifetime of the containers 100. Even when the assembly of the cartridge 200, reference solution containers 100, and waste bag 208 experiences varying external barometric pressures, it has been observed that the substantially constant partial pressures are maintained at least until the containers 100 are substantially drained of the reference solution. Maintenance of gas levels within the reference solution containers 100 is important to attain accurate calibration of blood-gas analyzers 300.

The reference solution containers 100 can be filled with reference solution according to a particular method involving several steps. First, a vacuum is applied to an empty reference solution container 100, evacuating the interior of the fluid bag 101. This is conventionally done with a vacuum pump, which is preferably coupled to the fluid bag 101 via the self-sealing fluid port (or valve) 104. Second, the vacuum pump is removed from the valve 104. Because the valve 104 is self-sealing (as described above), when the vacuum pump is removed from the valve 104, the fluid bag 101 remains reasonably sealed. Third, a fluid fitting is inserted into and unseals the valve 104, and the fluid bag 101 is filled with reference solution. Finally, the fluid bag 101 is "burped" or "expressed" to remove excess gases within the bag 101.

A manifold can be used to alternately couple the reference solution container 100 to the vacuum pump and the source of the reference solution. If such a manifold is used, the first and third steps can be performed without the second step.

Several embodiments of the present invention have been described. Nevertheless, it will be understood that various modifications may be made without departing from the spirit and scope of the invention. For example, the reference solution container 100 of the present invention can have a protective layer applied to external surface of the container 100 for added protection against bursting and puncturing. Furthermore, the reference solution container 100 may be filled to an internal pressure that is greater than the ambient atmospheric pressure. Accordingly, it is to be understood that the invention is not to be limited by the specific illustrated embodiment, but only by the scope of the appended claims.

What is claimed is:

1. A reference solution container for an analyzer for measuring gas levels in a fluid, the container comprising:
   a. a fluid vessel for holding a reference solution;
   b. a self-sealing fluid port, including a mechanically actuated two-way valve that allows filling of the fluid vessel and repeated accessing of the reference solution in the fluid vessel by an external device without a substantial change in a partial pressure of each gas in the reference solution and without appreciable leakage of the reference solution;
wherein the mechanically actuated two-way valve includes:
   a. a port body having a fluid communication path extending throughout the length of the port body, the port body having a fitting end for engaging the external device; and
   b. a self-sealing valve, located substantially within the fluid communication path, that substantially prevents fluid flow into and out of the fluid vessel unless the external device is engaging the self-sealing valve: and
wherein the self-sealing valve has a valve stem and a valve stop; wherein the fluid communication path has a sealing surface; and wherein the valve stop forces the valve stem against the sealing surface to substantially prevent fluid flow through the fluid communication path unless the external device is inserted into the fluid communication path and deflects the valve stem from the sealing surface.

2. A reference solution container for an analyzer for measuring gas levels in a fluid, comprising
   a. a fluid vessel for holding a reference solution; and
   b. a self-sealing fluid port for repeatedly accessing the reference solution in the fluid vessel by a fluid carrying device that is external to the reference solution container;
   c. wherein a partial pressure of each gas in the reference solution is maintained at a substantially constant level;
   d. the self-sealing fluid port including a port body having a fluid communication path extending throughout the length of the port body, the port body having (1) a fitting end for engaging the external device and (2) a self-sealing valve, located substantially within the fluid communication path, that substantially prevents fluid flow into and out of the fluid vessel unless the external device is engaging the self-sealing valve; and
   e. the self-sealing valve having a valve stem and a valve stop and the fluid communication path having a sealing surface, the valve stop forcing the valve stem against the sealing surface to substantially prevent fluid flow through the fluid communication path unless the external fluid carrying device is inserted into the fluid communication path and deflects the valve stem from the sealing surface.

3. A reference solution container for an analyzer for measuring gas levels in a fluid, the container comprising:
   a. a fluid vessel for holding a reference solution;
   b. a self-sealing fluid port, coupled to the fluid vessel, that allows filling of the fluid vessel and repeated accessing of the reference solution in the fluid vessel by an external device while maintaining a partial pressure of each gas in the reference solution at a substantially constant level for a period of at least 60 days; and
wherein the reference solution container has a use-life of at least 60 days during which the reference solution in the fluid vessel is repeatedly accessed and the partial pressure of each gas in the reference solution container is maintained at a substantially constant level.

4. The reference solution container of claim 3 wherein the use-life is at least 120 days.

5. The reference solution container of claim 3, further comprising a seal, applied to the self-sealing fluid port, that substantially increases the use-life of the reference solution container.

* * * * *